(12) United States Patent
Castro et al.

(10) Patent No.: US 6,878,456 B2
(45) Date of Patent: *Apr. 12, 2005

(54) POLYCRYSTALLINE TRANSLUCENT ALUMINA-BASED CERAMIC MATERIAL, USES, AND METHODS

(75) Inventors: Darren T. Castro, Woodbury, MN (US); Richard P. Rusin, Woodbury, MN (US)

(73) Assignee: 3M Innovative Properties Co., St. Paul, MN (US)

(*) Notice: Subject to any disclaimer, the term of this patent is extended or adjusted under 35 U.S.C. 154(b) by 39 days.

This patent is subject to a terminal disclaimer.

(21) Appl. No.: 10/034,642

(22) Filed: Dec. 28, 2001

(65) Prior Publication Data

US 2003/0125189 A1 Jul. 3, 2003

(51) Int. Cl.[7] .......................... B32B 9/00; A61C 13/00; A61C 7/00; A61B 19/02; A61B 3/00
(52) U.S. Cl. .................. 428/542.8; 428/220; 428/702; 433/228.1; 433/218; 433/229; 433/224; 433/217.1; 406/63.5; 264/604
(58) Field of Search ................................ 428/432, 701, 428/702, 542.8, 220; 433/228.1, 218, 225, 224, 217.1; 106/35; 423/592.1, 625; 206/63.5; 264/604

(56) References Cited

U.S. PATENT DOCUMENTS

| 2,926,422 A | 3/1960 | Wallshein |
| 3,026,210 A | 3/1962 | Coble |
| 3,181,240 A | 5/1965 | Kerhart et al. |

(Continued)

FOREIGN PATENT DOCUMENTS

| DE | 1 228 754 | 6/1967 |
| DE | 1 541 219 | 1/1970 |
| DE | 2 039 226 | 3/1971 |
| DE | 2 328 213 | 1/1974 |
| DE | 25 54 145 | 6/1977 |
| EP | 0 160 481 B2 | 11/1985 |
| EP | 0 161 831 B1 | 11/1985 |
| EP | 0 284 418 B1 | 3/1988 |
| EP | 0 284 418 A1 | 9/1988 |
| EP | 0 430 654 B1 | 11/1990 |
| EP | 1 070 484 A2 | 1/2001 |
| WO | WO 89/08085 | 8/1989 |
| WO | WO 93/07830 A1 | 4/1993 |
| WO | WO 01/13862 A1 | 3/2001 |
| WO | WO 01/15620 A1 | 3/2001 |

OTHER PUBLICATIONS

American Society of Testing Materials, "ASTM–D2805–95, Standard Test Methods for Hiding Power of Paints by Reflectometry," *Annual Book of ASTM Standards*, pp. 307–311 (1995).

American Society of Testing Materials, "ASTM–E384–99, Test Methods for Microhardness of Materials," *Annual Book of ASTM Standards*, pp. 409–432 (1999).

Bruch, "Preparation of Translucent Alumina From Powder," pp. 1–19.

Carniglia, "Reexamination of Experimental Strength–vs–Grain Size Data for Ceramics," *Journal of American Ceramic Society*, 1972; vol. 55, Issue 5: pp. 243–249.

(Continued)

*Primary Examiner*—Deborah Jones
*Assistant Examiner*—G. Blackwell-Rudasill
(74) *Attorney, Agent, or Firm*—Sean Edman

(57) ABSTRACT

A polycrystalline translucent aluminum oxide ceramic material having an average grain size of no greater than 1.0 micron and a Contrast Ratio value of less than about 0.7. The material can be in the form of a dental mill blank, dental prosthesis or other dental article or non-dental article.

61 Claims, 8 Drawing Sheets

U.S. PATENT DOCUMENTS

| | | | |
|---|---|---|---|
| 3,423,833 | A | 1/1969 | Pearlman |
| 3,464,837 | A | 9/1969 | McLean et al. |
| 3,541,688 | A | 11/1970 | McLean et al. |
| 3,578,744 | A | 5/1971 | Wildman |
| 3,732,087 | A | 5/1973 | Grossman |
| 3,842,503 | A | 10/1974 | Wildman |
| RE28,889 | E | 7/1976 | Wildman |
| 4,097,935 | A | 7/1978 | Jarcho |
| 4,216,583 | A | 8/1980 | Reynolds |
| 4,219,617 | A | 8/1980 | Wallshein |
| 4,264,541 | A | 4/1981 | Oda et al. |
| 4,285,732 | A | 8/1981 | Charles et al. |
| 4,310,306 | A | 1/1982 | Wallshein |
| 4,321,042 | A | 3/1982 | Scheicher |
| 4,322,206 | A | 3/1982 | Reynolds |
| 4,431,420 | A | 2/1984 | Adair |
| 4,460,336 | A | 7/1984 | Smith et al. |
| 4,544,359 | A | 10/1985 | Waknine |
| 4,575,805 | A | 3/1986 | Moermann et al. |
| 4,595,598 | A | 6/1986 | De Luca et al. |
| 4,681,538 | A | 7/1987 | DeLuca et al. |
| 4,797,238 | A | 1/1989 | Rhodes et al. |
| 4,837,732 | A | 6/1989 | Brandestini et al. |
| 4,878,840 | A | 11/1989 | Reynolds |
| 4,927,361 | A | 5/1990 | Smith et al. |
| 4,954,080 | A | 9/1990 | Kelly et al. |
| 4,968,459 | A | 11/1990 | Sernetz |
| 4,988,293 | A | 1/1991 | Collins et al. |
| 5,011,403 | A | 4/1991 | Sadoun et al. |
| 5,066,225 | A | 11/1991 | Forbes Jones et al. |
| 5,096,862 | A | 3/1992 | Mathers et al. |
| 5,231,062 | A | 7/1993 | Mathers et al. |
| 5,242,298 | A | 9/1993 | Sernetz |
| 5,244,849 | A | 9/1993 | Roy et al. |
| 5,358,402 | A | 10/1994 | Reed et al. |
| 5,376,606 | A | 12/1994 | Kim et al. |
| 5,380,196 | A | 1/1995 | Kelly et al. |
| 5,382,556 | A | 1/1995 | Takahashi et al. |
| 5,439,379 | A | 8/1995 | Hansen |
| 5,441,408 | A | 8/1995 | Moschik |
| 5,587,346 | A | 12/1996 | Zuk |
| 5,627,116 | A | 5/1997 | Zuk |
| 6,417,127 | B1 * | 7/2002 | Yamamoto et al. ......... 501/153 |
| 6,648,638 | B2 * | 11/2003 | Castro et al. ................... 433/8 |
| 2003/0031984 | A1 | 2/2003 | Rusin et al. |
| 2003/0165790 | A1 | 9/2003 | Castro et al. |

OTHER PUBLICATIONS

DIN EN 1184 "Materials and Articles in Contact with Foodstuffs: Test Methods for Translucency of Ceramic Articles" (Aug., 1997).

Ishitobi, et al., "Fabrication of Translucent $Al_2O_3$ by High Pressure Sintering," *Ceramic Bulletin*, 1977; vol. 56, No. 6: pp. 556–558.

Jacobson, "Fracture Characteristics, Hardness, and Grain Size of Five Polycrystalline Alumina Orthodontic Brackets," Thesis Abstract, *American Journal of Orthodontics and Dentofacial Orthopedics*, 2001, Jul.; vol. 120, Issue 1, pp. 92–93.

Jeppesen, "Some Optical, Thermo–Optical and Piezo–Optical Properties of Synthetic Sapphire," *Journal of the Optical Society of America*, 1958; vol. 48, No. 9: pp. 629–632.

Lynch, "Table 3–2 –Physical, Mechanical, Thermal, and Electrical Properties of Alumina," *Chemical Rubber Company Handbook of Materials Science*, 1974, pp. 358–361.

Malitson, "Refraction and Dispersion of Synthetic Sapphire," *Journal of the Optical Society of America*, 1962; vol. 52, No. 12: pp. 1377–1379.

Mendelson, "Average Grain Size in Polycrystalline Ceramics," *Journal of American Ceramic Society*, 1969; vol. 52, Issue 8: pp. 443–446.

Mizuta, "Preparation of High–Strength and Translucent Alumina by Hot Isostatic Pressing," *Journal of American Ceramic Society*, 1992; vol. 75, Issue 2: pp. 469–473.

Passmore, et al., "Strength–Grain Size–Porosity Relations in Alumina," *Journal of American Ceramic Society*, 1965; vol. 48, Issue 1: pp. 1–7.

Pham, "Fracture Characteristics, Hardness, and Grain Size of Five Polycrystalline Alumina Orthodontic Brackets," Master's Thesis, The Ohio State University, Columbus, Ohio, Title Page, Abstract, Table of Contents, pp. 1–47 (1999).

Rhodes, et al., "Hot–Working of Aluminum Oxide: II, Optical Properties," *Journal of American Ceramic Society*, 1974; vol. 58, No. 1–2: pp. 31–34.

Rhodes, et al., "Segregation of Magnesium to the Internal Surface of Residual Pores in Translucent Polycrystalline Alumina," *Journal of American Ceramic Society*, 1992; vol. 75, Issue 7: pp. 1796–1800.

Rhodes, et al., "Sintering of Translucent Alumina in a Nitrogen–Hydrogen Gas Atmosphere," *Journal of American Ceramic Society*, 2000; vol. 83, Issue 7: pp. 1641–1648.

Van Vlack, "Elements of Materials Science and Engineering," $6^{th}$ Edition, pp. 217–219, 1989.

ASTM Designation: E 112–96$^{e2}$, "Standard Test Methods for Determining Average Grain Size," American Standard Test Method International, West Conshohocken, PA, pp. 1–26 (May 10, 1996).

* cited by examiner

POLYCRYSTALLINE TRANSLUCENT ALUMINA-BASED CERAMIC MATERIAL, USES, AND METHODS

FIELD OF THE INVENTION

This invention relates broadly to polycrystalline alumina-based ceramic materials that have a relatively small grain size yet generally high translucency. Such materials are particularly useful in dental applications because of their ability to blend with or color-match the dentition surrounding the device, e.g., dental prosthesis.

BACKGROUND

Although performance and durability are highly desirable characteristics for dental replacement and repair work, for example, they alone are not the sole concern for practitioners and patients. Aesthetic value, or how dental materials look inside the mouth is just as desirable. For example, in prosthodontics and restorative dentistry, where tooth replacement, or prostheses, are custom made to fit in or on a tooth structure, there are instances where the restoration or repair can be seen from a short distance when the mouth is open. Thus in those instances, it would be highly desired that the dental material be nearly indistinguishable from adjacent tooth structure.

Prosthetics and restorative dentistry encompass the fabrication and installation of, for example, restoratives, replacements, inlays, onlays, veneers, full and partial crowns, bridges, implants, and posts. Conventional materials used to make dental prostheses include gold, ceramics, amalgam, porcelain and composites. In terms of aesthetic value, it is perceived that porcelains, composites and ceramics look better than amalgam and metals, since a prosthetic made from those nonmetals better matches or blends in with the color of adjacent natural teeth.

Various processes and procedures for creating or fabricating prostheses are now available to practitioners. Typically, a prosthesis is produced from a cast model made to replicate a dentition or through the use of computer automation is combined with optics, digitizing equipment, CAD/CAM (computer-aided design/computer aided machining) and mechanical milling tools. Fabrication of a prosthesis using a CAD/CAM device requires a "mill blank," a solid block of material from which the prosthesis is cut or carved. The mill blank may be made of ceramic material. Typical ceramic blanks generally require a practitioner or laboratory to hold a large inventory of blanks in various shades due to their opacity and pre-determined color/shading. It would therefore be advantageous to have a mill blank with no pre-determined color and the ability to blend with or color-match the dentition surrounding the milled prosthesis. Providing such a mill blank would eliminate the need for having a large inventory of blanks in varying colors and shades, and give the practitioner the flexibility to color-match a prosthesis with the use of just one mill blank.

SUMMARY OF THE INVENTION

The present invention is directed to a polycrystalline aluminum oxide ceramic material that has a desirable translucent quality. This is particularly advantageous for use in dental articles to achieve further cosmetic improvement by having a translucent quality that picks up the color of the underlying tooth to make the dental device (e.g., prosthesis) blend with the tooth. From the appearance standpoint, such translucent dental articles are a significant improvement over conventional nonmetallic dental articles that are opaque, since the visibility of the translucent dental articles is minimized when mounted on a tooth. Preferably, the material has a Contrast Ratio value of less than about 0.7.

The polycrystalline translucent ceramic material is formed by pressing a powder material, such as high purity aluminum oxide, into a desired shape, sintering the shaped material to provide closed porosity, and subjecting the sintered material to hot isostatic pressing to yield a single phase material having substantially zero porosity and an average grain size of no greater than 1.0 micrometer (i.e., micron). This small grain size contributes to a stronger material than conventional ceramic materials without detrimentally effecting translucency. This is surprising as small grain size is often considered to prevent relatively high translucency. Preferably, the material has a flexure strength of at least about 400 MPa.

Thus, the present invention provides a polycrystalline translucent aluminum oxide ceramic material having an average grain size of no greater than 1.0 micron and a Contrast Ratio value of less than about 0.7. Preferably, no greater than 10% of the grains of a polished surface of the material has a largest dimension greater than 1.0 micron.

The present invention also provides a dental mill blank that includes a polycrystalline translucent aluminum oxide ceramic material having an average grain size of no greater than 1.0 micron and a Contrast Ratio value of less than about 0.7. The blank is preferably mounted to a holder selected from the group of a stub, a frame, a collett, and a plate. Typically and preferably, the ceramic material of the mill blank has a tooth-like shade.

The present invention also provides a ceramic dental prosthesis that includes a polycrystalline translucent aluminum oxide ceramic material having an average grain size of no greater than 1.0 micron and a Contrast Ratio value of less than about 0.7. Preferably, the ceramic material of the prosthesis is coated at least partially with an aesthetic coating material selected from the group consisting of porcelain, glass, glass-ceramic, composite, resin ceramic composite, and combinations thereof. Typically and preferably, the dental prosthesis is selected from the group consisting of a crown, a coping, a bridge framework, a dental implant, a dental implant abutment, an inlay, an onlay, and a veneer.

The present invention also provides kits. A kit typically includes: a dental mill blank comprising a polycrystalline translucent aluminum oxide ceramic material having an average grain size of no greater than 1.0 micron and a Contrast Ratio value of less than about 0.7; and instructions for using the mill blank. The kit preferably further includes a component selected from the group consisting of a bonding agent, a milling lubricant, a color-matching composition suitable for use in the oral environment, an impression material, an instrument, a dental composite, a dental porcelain, an abrasive, and combinations thereof.

The present invention also provides a method for making a polycrystalline translucent aluminum oxide ceramic material having a grain size of no greater than 1.0 micron and a Contrast Ratio value of less than about 0.7 includes: providing an aluminum oxide powder; forming the powder into an article having a desired shape; sintering the shaped article to obtain a sintered article having closed porosity; and subjecting the sintered article to hot isostatic pressing to further densify and form a densified article comprising polycrystalline translucent aluminum oxide ceramic material having a grain size of no greater than 1.0 micron and a Contrast Ratio value of less than about 0.7.

In one embodiment, the step of forming the powder into an article having a desired shape involves forming a mill blank of ceramic material in a green stage. Preferably, the green-stage mill blank is carved into a desired shape prior to sintering the shaped article to obtain a sintered article having closed porosity.

In another embodiment of the method, the sintered article having closed porosity is carved into a desired shape prior to subjecting the sintered article to hot isostatic pressing to further densify. In an alternative embodiment of the method, the densified article is carved into a desired shape.

In yet other embodiments of methods of forming a polycrystalline translucent aluminum oxide ceramic material as described herein includes slurry casting or injection molding the aluminum oxide powder to form the powder into an article having a desired shape.

Also provided is a method for making a dental prosthesis that includes: providing a dental mill blank comprising a polycrystalline translucent aluminum oxide ceramic material having a grain size of no greater than 1.0 micron and a Contrast Ratio value of less than about 0.7; and carving the mill blank into a desired shape.

BRIEF DESCRIPTION OF THE DRAWINGS

Those skilled in the art may recognize that various modifications and additions may be employed in connection with the specific, presently preferred embodiments described and illustrated below in the accompanying drawings. As such, the invention should not be deemed limited to the particular embodiments set out in detail, but instead only by a fair scope of the claims that follow along with their equivalents.

DETAILED DESCRIPTION OF PREFERRED EMBODIMENTS

Figure 1:
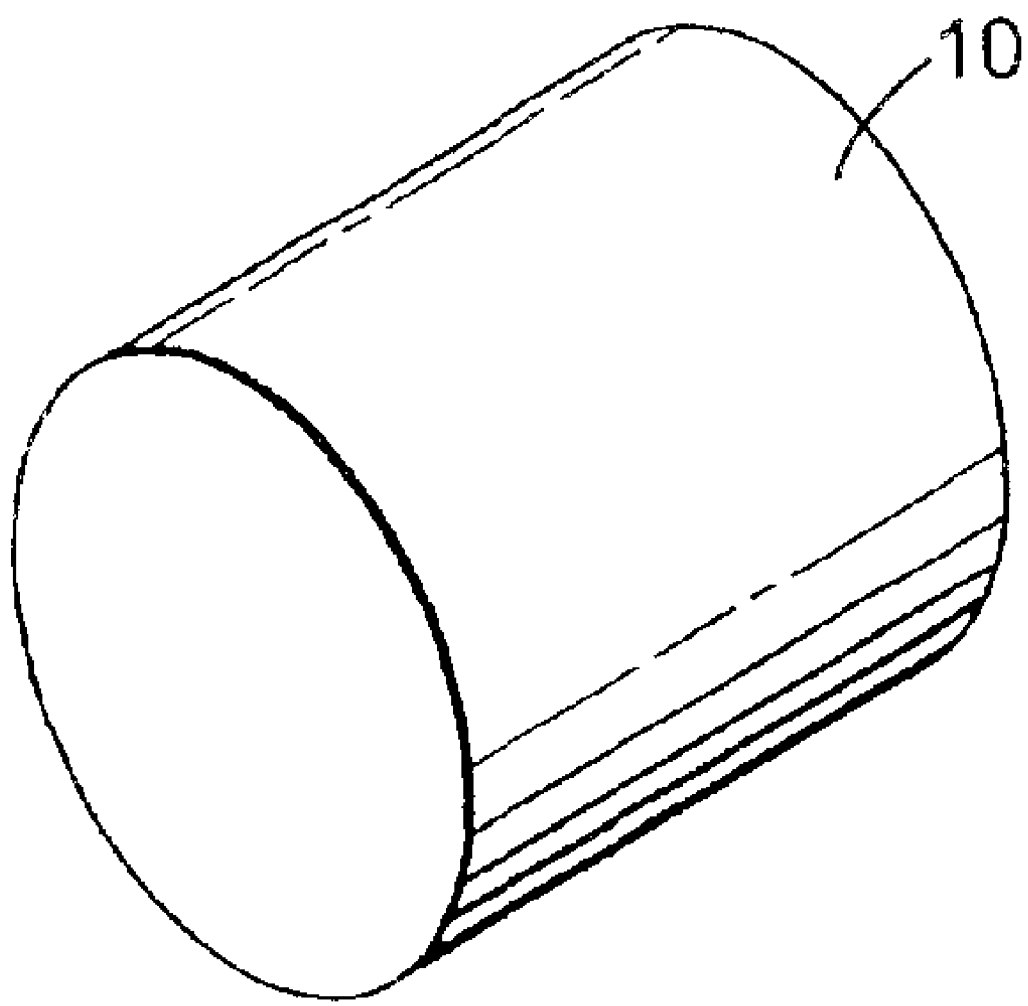
FIG. 1 is a perspective view of a crystalline ceramic mill blank according to one embodiment of the invention, where the mill blank is substantially cylindrical.

The present invention is directed to a polycrystalline aluminum oxide ceramic material that has an average grain size of no greater than 1.0 micrometer (i.e., micron). This small grain size contributes to a stronger material than conventional ceramic materials without detrimentally affecting translucency.

As a result of the high strength and translucency, the material of the present invention can be used in a variety of dental applications including dental mill blanks and prostheses such as crowns (full or partial), copings, bridge framework, implants, implant abutments, inlays, onlays, and veneers. Furthermore, it can be used in a variety of nondental applications including, for example, sodium vapor lamp envelopes, military armor, infrared radar domes, windows, and the like.

Ceramic Material

The ceramic material of the present invention is a translucent polycrystalline material. A "ceramic" refers to an inorganic nonmetallic material and "crystalline" refers to material that shows crystalline diffraction peaks when subjected to a bulk powder x-ray diffraction scan and is essentially free of glass. A polycrystalline material has a multiplicity of randomly oriented crystals joined at grain boundaries. Preferably, the ceramic material includes at least 99% polycrystalline ceramic having at least 99% theoretical density.

The ceramic utilized for the present invention is aluminum oxide. Aluminum oxide is desirable since it is strong, hard, colorless, and readily available. It is desirable that the aluminum oxide be of relatively high purity (preferably at least about 99.5% pure and more preferably at least about 99.9% pure) for generally high strength and significant freedom from chromatic effects.

Preferably, the ceramic material of the present invention is substantially nonporous to maintain a high degree of optical translucency. Furthermore, it is preferred that the average grain size of the ceramic material be no greater than 1.0 micrometer (i.e., micron). Preferably, no greater than 10% (i.e., number percent) of the grains as measured on a polished, etched surface of the material has a largest dimension (not actual grain size) greater than 1.0 micron. Preferably, no greater than 20% (i.e., number percent) of the grains as measured on a polished, etched surface of the material has a largest dimension greater than 0.9 micron.

This is significant because most conventional ceramic dental materials have a significantly larger average grain size (e.g., 10–50 microns) and/or a significantly larger amount (e.g., 50–90%) of the grains as measured on a polished, etched surface having a largest dimension (not actual grain size) of greater than 0.8 micron. The smaller grain size of the polycrystalline material of the present invention contributes to the significant strength of the material without detrimentally affecting the translucency.

Thus, the ceramic material of the present invention, and preferably, articles made therefrom, e.g., dental mill blanks, prostheses, and other nondental articles, are translucent. Translucency is the property of a specimen by which it transmits light diffusely without permitting a clear view of objects beyond the specimen and not in contact with it.

A translucent material is an advantage because a prosthesis, for example, formed from such a material effectively blends in with its surroundings and assumes the color of the underlying tooth and the teeth adjacent to it. This can provide improved aesthetics as compared to more opaque materials. For example, a prosthesis, restoration, or repair placed in a location readily seen when a patient opens his or her mouth would be more aesthetically pleasing if it were nearly indistinguishable and unnoticeable.

Particularly desirable materials should be neutral, and neither add color to the light passing through nor subtract color by appreciable absorption. Thus, a practitioner can easily color-match a prosthesis, for example, with the color and shade of the dentition that surrounds the prosthesis. This can lead to an elimination of the need for a practitioner or laboratory to carry a large range of pre-colored materials, e.g., mill blanks.

The ceramic material of the present invention is preferably an alpha aluminum oxide. Aluminum oxide is particularly desirable since its optical transmittance is substantially constant throughout the visible spectrum and it therefore does not change the color of light passing through.

In order for a dental article (e.g., prosthesis) to assume the color of the underlying tooth, it is important that sufficient light seen from the front surface of the article attached to the tooth be light that has been transmitted from the tooth surface, and that the tooth color is not overwhelmed by light backscattered from optical irregularities within the article. In other words, a substantial amount of the incident light should pass through the article, albeit diffused, to the base for reflection off of the tooth surface, and then be retransmitted through the article to be emitted from the front surface. Since the article is translucent rather than transparent, a portion of the light is backscattered by the internal grain boundaries of the ceramic as well as by impurities in the article. The backscattering due to impurities is preferably minimized since such backscattered light tends to be white and will almost invariably be different from the tooth color. Further, by using a translucent ceramic material, many of the optical properties of the tooth are mimicked.

It is significant that the translucence be a bulk property of the material rather than a surface effect. Some light diffusion can be obtained by roughening a surface as, for example, with frosted glass. This is not completely satisfactory in a dental article, however, since the surface is continually wet, and the principal change in the index of refraction occurs at the air-liquid interface, which is nearly smooth. Further, it is undesirable to have roughened surfaces on dental articles, which can cause discomfort in the mouth. Also, rough surfaces may also have imperfections, which serve as a source for initiation of cracks. Since ceramics do not have the ductility of metals, roughness can significantly degrade strength.

The Contrast Ratio value of a material is a measure of the opacity of the material as a ratio of the reflectance through the material on a black substrate to that of an identical material on a white substrate. Contrast Ratio values can be measured using a technique based on Section 3.2.1 of ASTM-D2805-95, modified for samples of about 1 millimeter (mm) thick. This test method is provided in the Examples Section. Lower values of Contrast Ratio indicate greater levels of light transmissivity.

Ceramic materials, and articles made from such materials, according to the present invention have a Contrast Ratio value of less than about 0.7, preferably less than about 0.6, even more preferably less than about 0.5, and most preferably less than about 0.4.

The transmittance of a material is a measure of the opacity of the material as a percentage of light at a particular wavelength that passes through the material. Percent transmittance can be measured using a technique based on the published standard method DIN EN 1184, modified for samples of about 1 millimeter (mm) thick. The samples can be evaluated wet or dry. This test method is provided in the Examples Section.

Ceramic materials, and articles made from such materials, according to the present invention preferably have a wet transmittance of at least about 40% at about 550 nm. More preferably, the wet transmittance is at least about 50% at about 650 nm. Alternatively stated, the wet transmittance curve over a range of about 475 nm to about 650 nm has an integrated area of greater than about 70% T-nm (i.e., units of % Transmittance×Wavelength (nm)).

The ceramic material of the present invention, and articles formed therefrom, e.g., dental mill blanks and prostheses, also offer other desirable properties such as high flexure strength. Flexure strength can be measured according to the test method described in the Examples Section. It is desirable that a dental material used for prostheses and restorations have high strength and reliable mechanical properties when machined into a complex shape and subjected to complex stresses.

Flexure strength indicates the ability for a ceramic material, which may be in the form or a mill blank, and articles formed therefrom, to withstand forces exerted on dentition and restoration. Materials of the present invention exhibit excellent flexure strength. Preferably, they possess a flexure strength of at least about 400 MPa (megapascals), more preferably at least about 500 MPa, and most preferably at least about 600 MPa. Having these strengths ensures that dental articles according to the invention are durable under typical use conditions.

Although the ceramic material of the present invention is preferably at least about 99.5% pure (by weight), and more preferably at least about 99.9% pure, if desired, additives may be included in the ceramic material. These include dopants, colorants, and processing additives. Colorants can be used to achieve desired shades of teeth. Examples of suitable colorants include iron oxide, rare earth oxides, and bismuth oxide. Processing additives include, for example, sintering aids such as magnesium oxide, yttrium oxide, zirconium oxide, hafnium oxide, and calcium oxide. Various combinations of such additives can be used if desired. If used, such additives are present in an amount up to about 0.5 percent by weight (wt-%).

Methods of Making Ceramic Material

Various methods of shaping the ceramic material of the present invention may be employed, including die pressing, slurry casting, injection molding, extrusion processes, and rapid prototyping. The resultant material can be in the final desired shape or it can be in the form of a mill blank that is subjected to further machining or copy milling, for example. These processes are well known for their use in making ceramic materials.

Generally, a method for making a polycrystalline translucent aluminum oxide ceramic material as described herein includes: providing an aluminum oxide powder; forming the powder into an article having a desired shape; sintering the shaped article to obtain a sintered article having closed porosity; and subjecting the sintered article to hot isostatic pressing to further densify and form a densified article that includes polycrystalline translucent aluminum oxide ceramic material. In one embodiment, forming the powder into an article having a desired shape includes forming a mill blank that includes ceramic material in a green stage. The green-stage mill blank can be carved into a desired shape prior to sintering the shaped article. Alternatively, the sintered article (mill blank) can be carved prior to subjecting it to hot isostatic pressing to further densify. Alternatively, the densified article (mill blank) can be carved into a desired shape.

A preferred method of making the ceramic material of the present invention involves initially combining powdered aluminum oxide in water and treating to deagglomerate the particles. This treatment is preferably done using ultrasonication. Typically, a sample of aluminum oxide is combined with water (generally distilled or deionized water) to form a slurry of about 25 wt-% to about 40 wt-% solids and sonicated for a period of time effective to deagglomerate the particles (typically about 1 to about 3 hours). If desired, the pH of the slurry can be adjusted for enhancing the dispersibility of the powder using, for example, ammonium citrate.

The aluminum oxide powder is preferably at least about 99.5% pure, more preferably at least about 99.9% pure, and most preferably at least about 99.99% pure. Typically, the powder includes particles having an average particle size (e.g., an average diameter) of no greater than about 0.5 micron and a surface area of greater than about 10 square meters per gram ($m^2/g$), preferably greater than about 14 $m^2/g$. Preferably, submicron size particles are used. This provides an active sintering process and allows one to achieve substantially theoretical density in the sintered, hot isostatic pressed compact.

This material is then typically combined with a small amount of a temporary organic binder, such as an acrylic binder or paraffin wax, optionally with a plasticizer such as polyethylene glycol, and then shaped. Preferably, about 5 weight percent (wt-%) to about 13 wt-% binder is applied by well-known methods (e.g., milling, spray drying) to the ceramic powder. Such binder is generally removed in subsequent processing operations. The mixture is typically then pressed into cylindrical pellets (typically of a diameter of about 10 mm to about 50 mm and height of about 1 cm to about 100 cm) at room temperature under a pressure of about 100 MPa to about 350 MPa. Preferably, the pressed pellets are then subjected to cold isostatic pressing ("CIPing") at room temperature and a pressure of about 100 MPa to about 350 MPa. This material is typically referred to as the "green stage" of the material with binder and is relatively porous (e.g., at least about 25% porosity).

This green stage material is then heated under conditions to remove substantially all the organic binder. Typically, this occurs at a temperature of about 600° C. to about 700° C., preferably at atmospheric pressure, and for a time of about 1 hour to about 3 hours. After removal of the binder, the material is also often referred to as the "green stage." Preferably, the "green density" of the material at this stage is at least about 58% of full density.

The green stage material, with or without binder (preferably without binder), can be subjected to processes that form the material into a desired shape before further densification.

This green stage material without the binder is then subjected to heating (i.e., firing or sintering) to densify the material. Typically, heating involves a multi-step process. For example, the material can be sintered at a temperature of about 1200° C. to about 1300° C. in air for about 1 hour to about 3 hours. At this stage, the sintered material is preferably at about 96–98% of full density and generally has a bright white, opaque appearance.

This sintered material, which typically includes closed pores, may also then be heated under conditions to further densify the material and remove substantially all the pores. Typically, this occurs at a temperature of about 1200° C. to about 1450° C. for a time of about 1 hour to about 3 hours and typically results in a material of very low porosity. This final heating step preferably includes hot isostatic pressing ("HIPing") to accelerate the heating process and achieve full translucency. Isostatic pressure (provided by an inert gas, typically argon) is applied while the material is heated to the HIPing temperature. The combination of high temperature and high pressure compacts the material to have substantially zero porosity. U.S. Pat. No. 4,954,080 (Kelly et al.) provides further discussion as to hot isostatic pressing aluminum oxide. Preferred HIPing conditions include a temperature of about 1200° C. to about 1300° C. for about 30 minutes to about 120 minutes under about 100 MPa to about 210 MPa of an inert gas (e.g., argon). The aluminum oxide ceramic material is preferably fully sintered and HIPed to achieve greater than about 99.8% of the theoretical density of the ceramic material.

Significantly, the process of the present invention can be carried out in air or an inert gas without the use of any sintering additive. Sintering aids can be used, if desired, in an amount up to about 0.5 wt-% total. Examples of suitable sintering aids include magnesium oxide, yttrium oxide, zirconium oxide, hafnium oxide, and calcium oxide, which can be used in combination.

Mill Blanks

The dental mill blanks of the present invention may be made in any desired shape or size, including cylinders, bars, cubes, polyhedra, ovoids, and plates. Herein, a mill blank is an article that is subjected to further shaping processes to create the desired product. Although this may occur after the ceramic material of the mill blank has been fully densified (preferably greater than about 99.5%), it can occur when the ceramic material is in a less dense stage (e.g., at about 96–98% of full density) or in the green stage, with or without binder, or at a less dense stage. If the ceramic material of a mill blank is in the green stage or at 96–98% of full density during shaping (e.g., carving), the resultant product is then typically subjected to further densification as described above.

Referring now to the drawing, FIG. 1 shows a preferred embodiment of a mill blank, where blank 10 is substantially cylindrical. Alternatively, the blanks can come in a variety of shapes and sizes. The ceramic material of the invention, which can be in the form of a dental mill blank, can be readily formed or milled into a variety of dental articles such as restoratives, replacements, inlays, onlays, veneers, full and partial crowns, bridges, implants, implant abutments, and posts. Preferred dental articles are prosthetics such as crowns, copings, bridge framework, implants, implant abutments, inlays, onlays, and veneers.

Various means, e.g., carving means, of milling the mill blanks of the present invention may be employed to create custom-fit dental prostheses having a desired shape. As used herein, "carving" means abrading, polishing, controlled vaporization, electronic discharge milling (EDM), cutting by water jet or laser or any other method of cutting, removing, shaping or milling material. The mill blank can be mounted to a holder, for example, a stub, a frame, a collet, or a plate during carving if so desired.

It is preferable that the prosthesis be milled quickly without imparting undue damage. This can be done by hand using a hand-held tool or instrument. An example of a hand-held tool that can be used to carve a prosthesis from a mill blank of the invention is that available under the trade designation DREMEL MultiPro, which is a variable speed rotary tool with diamond points (Dremel, Inc., Racine, Wis.).

New and more efficient methods, however, are emerging whereby computer automated equipment is programmed to machine a blank into a precise prosthesis. This is frequently referred to as "digital dentistry," where computer automation is combined with optics, digitizing equipment, CAD/CAM (computer-aided design/computer aided machining) and mechanical milling tools. Examples of such a computer-aided milling machine include those machines commercially available under the trade designations CEREC 2 machine (available from Sirona Dental Systems, Bensheim, Germany), VITA CELAY (available from Vita Zahnfabrik, Bad Säckingen, Germany), PRO-CAM (Intra-Tech Dental Products, Dallas, Tex.), and PROCERA ALLCERAM (available from Nobel Biocare USA, Inc., Westmont, Ill.). U.S. Pat. Nos. 4,837,732 (Brandestini et al.) and U.S. Pat. No. 4,575,805 (Moermann et al.) also disclose the technology of computer-aided milling machines for making dental prostheses. These machines produce dental prostheses by cutting, milling, and grinding the near-exact shape and morphology of a required restorative with greater speed and lower labor requirements than conventional hand-made procedures.

By using a CAD/CAM milling device, the prosthesis can be fabricated efficiently and with precision. During milling, the contact area may be dry, or it may be flushed with or immersed in a lubricant. Alternatively, it may be flushed with an air or gas stream. Suitable liquid lubricants are well known, and include water, oils, glycerine, ethylene glycols, and silicones. After machine milling, some degree of finishing, polishing and adjustment may be necessary to obtain a custom fit in to the mouth and/or aesthetic appearance.

For cost and time efficiency, it is desirable to have the ability of rapidly milling a complete prosthesis from a crystalline ceramic mill blank within a short time period. The mill blanks of the present invention provide such a capability, where a restoration of a desired shape, such as a full crown, for example, can be milled in a period of less than about 3 hours. Preferably a complete prosthesis can be milled in less than about 2 hours; more preferably in less than about 1 hour; and most preferably in less than about ½ hour. Rapid millability is especially advantageous in instances where a patient desires to be treated in a single appointment and a practitioner has access to a CAD/CAM milling machine. In those situations, it is conceivable that the practitioner can make a complete prosthesis while a patient sits chair-side.

A milled dental prosthesis can be attached to the tooth or bone structure with a wide variety of bonding agents. Examples include glass ionomer cements, resin cements, zinc phosphate, zinc polycarboxylate, compomer, or resin-modified glass ionomer cements.

Adhesion may be enhanced by coating the milled prosthesis with silica and using silane-coupling agents. Alternatively, to enhance bonding, retentive grooves or undercuts may be carved into the bonding surfaces of the prosthesis.

The use of a translucent material for a mill blank allows external tailoring of the appearance of the restoration by modifying both the color of the luting or bonding agent and color/shading of the inner surface of the restoration. For example, use of certain types of luting or bonding composites or cements can provide coloration to or in combination with a prosthesis milled from a mill blank according to the invention. This can be accomplished through custom shading or color-matching, whereby a colored composition (cement, paste, gel, etc.) suitable for use in an oral environment is used to adhere the prosthesis to the underlying tooth structure. The result is that the appearance of the milled prosthesis will closely match the surrounding dentition. Preferred composites are available under the trade designations 3M OPAL Luting Composite and 3M RELYX ARC Adhesive Resin Cement (3M Co., St. Paul, Minn.). Alternatively, a color or shading composition may be used to add coloration or shading by coating or painting the composition directly onto the underlying structure of the prosthesis, or onto a surface of a milled prosthesis.

Optionally, additional material can be added to the milled prosthesis for various purposes including repair, correction, or enhancing aesthetics. The additional material may be of one or more different shades or colors and may be material made from composite, ceramic, metal, glass or a glass-ceramic such as feldspathic porcelain. In a preferred method, a resin ceramic composite or a feldspathic porcelain is used. For example, a further use of the mill blanks of the present invention is to mill the blank into substructure, such as a coping or bridge framework, upon which additional material such as a composite or porcelain may be added, built-up or bonded, resulting in a highly aesthetic restoration. A preferred embodiment involves applying an aesthetic coating of a ceramic, glass, glass-ceramic, composite, or combination thereof. Upon addition of material to the carved or milled blank, a practitioner or laboratory technician may choose or need to manually change the shape of the prosthesis. This re-work is generally performed to provide a custom fit into a patient's dentition. Optionally, or as a consequence of re-work, the practitioner or laboratory may choose to "finish" the outer surface of the milled blank. Finishing may include surface modifications such as polishing, painting, luting, buffing, grinding, glazing, and applying gloss or overcoat.

The ceramic mill blank of the invention may be provided in kit-form, where one or more blanks are placed into a multiple-unit kit, along with instructions for using the blanks. Preferably, a color-matching composition such as a luting or bonding agent is provided in a multiple-unit kit. A milling lubricant compatible with a milling process and the mill blank may also be provided in the multiple-unit kit.

Besides one or more bonding agents, one or more milling lubricants, the kits of the present invention can include one or more color-matching compositions suitable for use in the oral environment, one or more impression materials, one or more instruments, one or more dental composites, one or more dental porcelains, one or more abrasives, or various combinations thereof.

Optionally, multiple shades of the mill blanks may be provided in a kit. For example, one each of a light shade, a medium shade, and a dark shade blank may be placed into a kit to provide a practitioner with blanks that can be milled into prostheses and readily blend in with a range of shades.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are by weight and all molecular weights are weight average molecular weight.

Test Methods

Hardness

The average microhardness of example materials was measured by mounting processed ceramic parts in mounting resin (obtained under the trade designation "EPOXIDE" from Buehler Ltd., Lake Bluff, Ill.). More specifically, materials were secured in a 3.18-cm (1.25-inch) diameter, 1.9-cm (0.75-inch) tall cylinder of the resin. The mounted sample was polished using diamond lapping film (obtained under the trade designation "IMPERIAL DIAMOND LAPPING FILM" from the 3M Company, St. Paul, Minn.), with the final polishing step using a 0.5 micrometer diamond film to obtain polished cross-sections of the samples.

Hardness measurements were made using a conventional microhardness tester obtained under the trade designation "MITUTOYO MVK-VL" from Mitutoyo Corp. of Tokyo, Japan) fitted with a Vickers indenter using a 500-gram indent load. The hardness measurements were made according to the guidelines stated in ASTM Test Method E384 Test Methods for Microhardness of Materials (1991). The reported hardness values are an average of 10 measurements.

Flexure Strength

Test bars measuring 2.5-mm wide×1.5-mm thick×12.0-mm long, with 0.15±0.05 mm×45° chamfers, were machined by Chand Kare Technical Ceramics, Worcester, Mass. The test bars were soaked in distilled water at 37° C. for 24 hours prior to testing. A 3-point beam bend test configuration with a span of 10.0 mm was employed. The crosshead test speed was 0.75 mm/min. An Instron 4505 test frame (Instron Corporation, Canton, Mass.) was utilized. Flexure Strength results were reported in units of MPa as minimum, maximum, and average strength values. Average strength values are an average of 5 measurements.

Contrast Ratio

In order to quantitatively assess translucency of a material, ceramic discs with 2 parallel flat surfaces, a thickness of 1.0±0.03 mm, and various diameters ranging from 12 to 15 mm were prepared by cutting discs at a speed of 2500 rpm and a load of 1000 grams using a Buehler Isomet 2000 Precision Saw (Buehler Co., Lake Bluff, Ill.) and a Buehler Series 15-LC diamond wafering blade (15.24 cm, #11-4276). Both surfaces (front and back of disc) were made uniform by passing them back and forth 10 times over an approximately 7.6-cm path along 600-grit sandpaper (3M Wetordry Tri-M-Ite, #438Q; 3M Company, St. Paul, Minn.). Distilled water was used as a lubricant and to rinse the sample discs.

ASTM-D2805-95 test method was modified to measure the Contrast Ratio (or opacity) of the discs. Y-tristimulus values for the discs were measured on an Ultrascan XE Colorimeter (Hunter Associates Laboratory, Reston, Va.) with a 0.953-cm aperture using separate white and black backgrounds. The D65 Illuminant was used with no filters for all measurements. A 10° angle of view was used. The Contrast Ratio or opacity, C, was calculated as the ratio of the reflectance through a material on a black substrate to that of an identical material on a white substrate. Reflectance is defined as equal to the Y-tristimulus value. Thus, C=RB/RW, where RB=reflectance through a ceramic disc on a black substrate and RW=reflectance through the same disc on a white substrate. Reported Contrast Ratio values are the results of single measurements. Lower values are indicative of greater translucency (i.e., transmission of light).

Translucency of Small Samples (Wet Transmittance)

The translucency of small test samples, e.g., the size of an orthodontic bracket, was quantitatively measured according to the following method that is a modification of the published standard method, "Materials and Articles in Contact with Foodstuffs: Test Methods for Translucency of Ceramic Articles"; DIN EN 1184; August, 1997. Small test samples, for example ceramic orthodontic brackets, were cleaned with ethanol, and dried in a stream of anhydrous nitrogen. The dried samples were sputter coated with approximately 40 nm of Au/Pd, and mounted into 2.54-cm phenolic rings using Buehler-Two Part Epoxy (Buehler Co., Lake Bluff, Ill.). Special attention was paid to the mounting orientation of the samples to ensure that a representative cross-section of the sample would be created, and that any non-alumina materials (such as glass frit coatings) would be removed during the sectioning process. The mounts were allowed to cure overnight at room temperature. The cured mounts were sectioned to between approximately 1.5 to 5-mm widths with a Struers Accutom-50 high-speed diamond saw.

Following sectioning, samples were hand ground on 600-grit SiC grinding paper on a Buehler Ecomet 4 (Buehler Co., Lake Bluff, Ill.). A Fowler micrometer caliper was used to monitor progress of material removal. Once samples were ground to within approximately 20–30% of ideal width (1000 $\mu$m), samples were polished using 3M Imperial Diamond Lapping Film (9 $\mu$m) placed on a flat table. Small amounts of water and Buehler Metadi Fluid (diamond extender) were used as lubricants for the grinding and polishing steps. Final widths of all samples through the plane of interest were 1000 $\mu$m (+/−2%).

The test procedure used was based on DIN EN 1184—1997 "Materials and articles in contact with foodstuffs: Test methods for translucency of ceramic articles," (August, 1997). This DIN standard procedure was modified as follows:

Section 4.2.1 Photometer—a spectrophotometer rather than a photometer was used. Visible light microspectrophotometry was done using a Leica Orthoplan Microscope, an 16×/0.30NA objective, 0.30 substage condenser, and a Leica MPV-Combi spectrophotometer.

Section 4.3 Preparation of test specimen. For the data reported herein, the specimens were 1.00-mm thick rather than 2.00-mm thick.

Measurements were made for each sample by utilizing the 16×/0.30NA objective to produce a light source with a half angle of 17 degrees. A "wet" reading was taken by submerging (in immersion oil) each sample in a well slide. This well slide was made by the 3M Glass Shop and consisted of a standard microscope slide with 0.6-cm glass cylinder attached to create a flat bottom well. The operating conditions of the Leica MPV were: scan range of 350 nm to 800 nm, 2× integration, 300-hz filter edge, and 4 scan averaging. Four locations on the polished bracket were scanned (4 scans at each location) and the results were averaged in the reported data. The system was calibrated following the manufacturers instructions. The calibration condition for 100% transmission was defined as the well slide filled with immersion oil.

Grain Size

The average grain size of an alumina test sample was determined from Scanning Electron Microscopy (SEM) images. Prior to scanning, the sample was mounted and polished as described above for hardness testing. Following polishing, the sample was removed from the mounting media, cleaned and immersed for 1 minute in an aqueous supersaturated borax (sodium borate) solution at 80° C. The sample, coated with the sodium borate solution, was then heated at 5° C./min to 900° C. and soaked at 900° C. for 30 minutes in flowing air. The borax solution reacted with the alumina to form a glass at the polished surface grain boundaries. Upon cooling, the polished surface was etched for 1 minute in a boiling 12% HCl acid solution to remove the resultant glass. This procedure served to reveal the grain structure of the sample without doing a higher temperature thermal etch that might have altered the existing microstructure.

Following rinsing with deionized water and drying in air, the sample was mounted on aluminum SEM stubs and coated with a thin layer of Au/Pd. The samples were viewed at an angle normal to the polished surface using a scanning electron microscope (obtained under the trade designation "JEOL Model JSM 6400" from JEOL, Ltd. of Akishima, Japan). The average grain size of the sample was determined using the linear-intercept method on the plane of polish as described by M. I. Mendelson, "Average Grain Size in Polycrystalline Ceramics," *Journal of the American Ceramic Society*, 52 [8] 443–446 (1969), using a proportionality constant (k) of 1.56, which relates the average grain size (D) to the average intercept length (L): D=1.56 L.

Starting Materials

Alumina Powder

Starting alumina ($Al_2O_3$) powder was obtained from Taimei Chemicals Co., Tokyo, Japan and designated TM-DAR. The powder was reported by the manufacturer to have a nominal composition of 99.99 wt-% $Al_2O_3$, with the balance being comprised of impurities of the following metals/oxides: Na (5 ppm), K (1 ppm), Fe (4 ppm), Ca (1 ppm), Mg (1 ppm) and Si (2 ppm). The nominal surface area of this powder was 14.8 $m^2$/g with an average particle size of 0.18 μm (manufacturer's data).

Example 1

Polycrystalline Translucent Alumina Preparation

Initial Alumina Powder Treatment

The TM-DAR alumina powder as received was de-agglomerated and prepared for subsequent processing as follows. The powder was mixed with distilled water (in an amount equal to approximately 42% by weight of the powder) and ammonium hydrogen citrate powder (Sigma-Aldrich Chemical Company, St. Louis, Mo.) (in an amount equal to approximately 0.45% by weight of the powder) in a polyethylene bottle. The bottle was placed in an ultrasonic water bath at room temperature and the powder slurry was ultrasonicated for 2 hours. Following sonication, ammonium hydroxide (Alfa Aesar, Ward Hill, Mass.) was added in an amount equal to approximately 0.3% by weight of the powder to raise the pH of the solution. The resulting slurry was then further prepared for spray drying by adding DURAMAX B-1000 binder, an acrylic resin manufactured by Rohm and Haas Company, (Philadelphia, Pa.). Prior to adding the binder (in an amount equal to approximately 9.7% by weight of the powder), the binder was diluted with approximately 2 parts distilled water to 1 part binder. Next, Carbowax Polyethylene Glycol 400, a plasticizer from Union Carbide, (Danbury, Conn.) was added to the slurry in an amount equal to approximately 1.1% by weight of the powder. Prior to adding the Carbowax 400 to the powder-binder slurry, the Carbowax 400 was diluted with approximately 4.5 parts distilled water to 1 part Carbowax 400. The resulting slurry was mixed with a magnetic stirbar and spray dried (Buchi Mini Spray Dryer B-191, obtained from Brinkman Instruments, Westbury, N.Y.; Inlet Temperature=195° C., Outlet Temperature=100° C.) to produce a fine, free-flowing powder suitable for further processing.

Powder Formation Processing

The free-flowing alumina powder was uniaxially pressed into 10.25-g cylindrical pellets by using a die with a diameter of 16.6 mm and an applied pressure of approximately 310 MPa. (Press was obtained from Carver Laboratory Press, Model M, Carver, Inc., Wabash, Ind.). The resulting pellets were then cold isostatically pressed (CIPed) at approximately 170 MPa (Model #IP4-22-60, Autoclave Engineers, Erie, Pa.).

Binder Burn-out Processing

The CIPed pellets (or ceramic parts of other shapes) were burned out in air at 690° C. for 1 hour to remove the organic components added to facilitate dispersion and spray drying. (The ramp rate to 690° C. was approximately 1° C./min. After a 1 hour soak at 690° C., the furnace power was shut-off and the furnace cooled at its own rate.) Following binder burnout, the ceramic parts typically had a "green" (non-sintered) density in excess of 58% (on a theoretical density basis of 3.98 $g/cm^3$).

Sintering Processing

Following binder burn-out processing, the ceramic parts were sintered at 1235° C. in air for 2 hours with ramp and cool rates of 20° C./min. This pressureless, sintering process typically produced ceramic parts having a density of approximately 3.83 $g/cm^3$, approximately 96% of their theoretical density. At approximately 96% of full density, these ceramic parts were bright white and opaque in appearance. Additionally, the ceramic parts had reached closed porosity at this point in the process, as indicated by near equivalence in their dry weights and saturated weights as determined by the Archimedes density technique Once closed porosity was reached, the sintered ceramic parts were capable of being hot isostatically pressed (HIPed) without encapsulation.

Hot Isostatically Pressed Powder Processing

Figure 2:
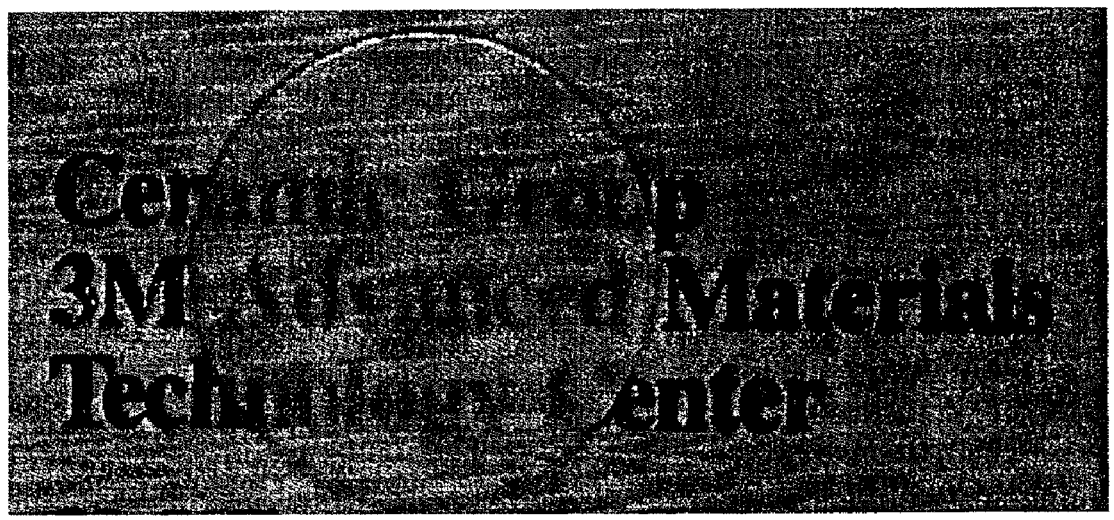
FIG. 2 depicts a qualitative translucency assessment of Example 1 ceramic material.
Figure 3:
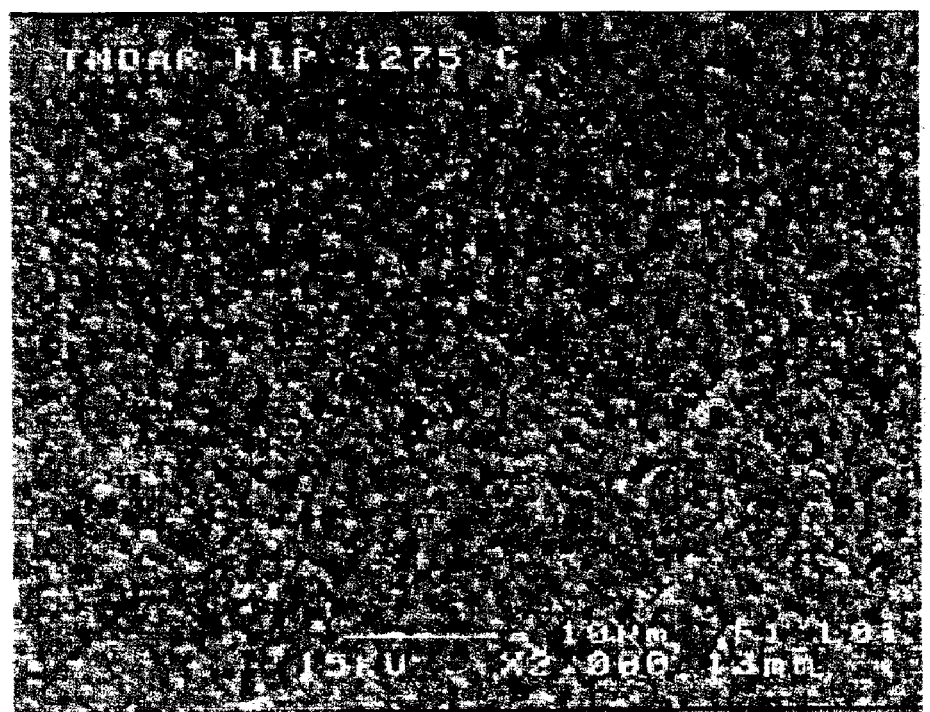
FIG. 3 is a Scanning Electron Microscopy (SEM) image (2000x) of a cross-section of the Example 1 ceramic material.

The sintered ceramic parts were HIPed at 1275° C. for 65 minutes with an applied argon pressure of 207 MPa and heating ramp rates of 20° C./min below 1200° C. and 13° C./min above 1200° C. The cooling rate was approximately 25° C./min. The resulting ceramic parts (Example 1 Translucent Alumina) had a final density of approximately 3.98 $g/cm^3$ (essentially 100% of its theoretical density, based on atomic packing considerations) and were translucent in appearance. A qualitative assessment of Example 1 translucency was made as shown in FIG. 2, demonstrating that printed text could readily be read through a 1-mm thick disc of the material. The average grain size of the Example 1 Alumina was measured according to the test method provided herein and was determined to be 0.8 μm. A Scanning Electron Microscopy (SEM) image (2,000×) of the Example 1 Alumina is shown in FIG. 3. The hardness of the Example 1 Alumina was measured according to the test method provided herein and was found to be 22.1±0.5 GPa.

Example 2

Polycrystalline Translucent Alumina Preparation

Figure 4:
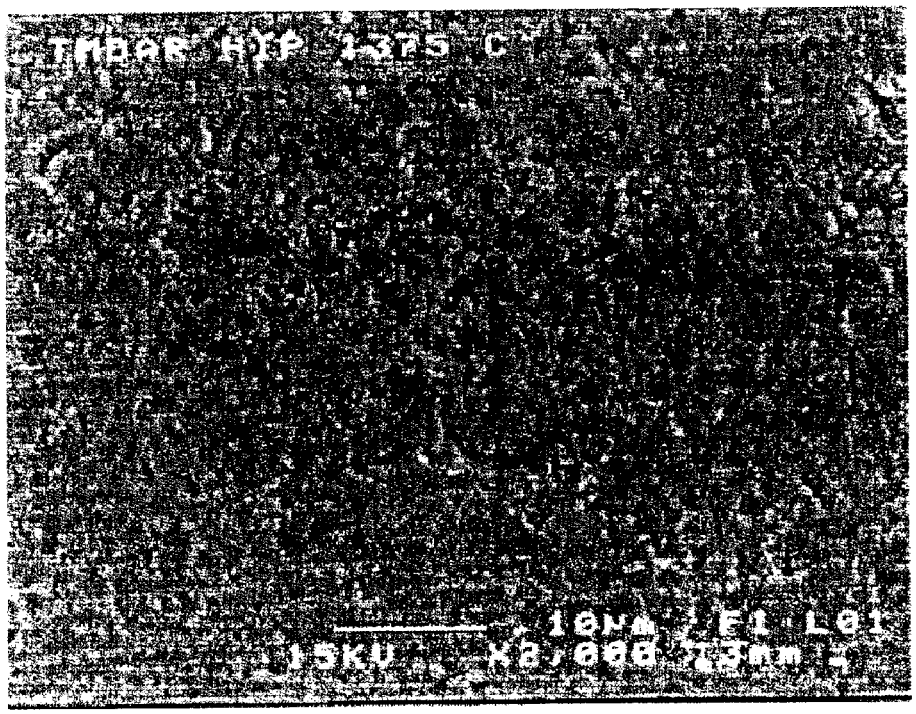
FIG. 4 is an SEM image (2,000x) of a cross-section of the Example 2 ceramic material.

The TM-DAR alumina powder was processed as described for Example 1, except that the sintered pellets (or ceramic parts) were HIPed at 1375° C. (as compared to 1275° C. in Example 1) for 30 minutes (as compared to 65 minutes in Example 1). The resulting ceramic parts (Example 2 Translucent Alumina) had a final density of approximately 3.99 $g/cm^3$ (slightly greater than 100% of what was believed to be its theoretical density) and were translucent in appearance, appearing visually to be of a similar translucency to Example 1 Alumina. The average grain size of the Example 2 Alumina was measured according to the test method provided herein and determined to be 0.9 μm. A Scanning Electron Microscopy image (2,000×) is shown in FIG. 4. The hardness of the Example 2 Alumina was measured according to the test method provided herein and was found to be 21.7±0.7 GPa.

Example 3

Polycrystalline Translucent Alumina Preparation

In order to prepare larger quantities of the polycrystalline translucent alumina and to ensure that all parts were uniformly processed, the following modified process was employed.

The TM-DAR alumina powder as received was processed as described for Example 1, except that the binder burn-out at 690° C. was extended to 2 hours (from 1 hour) and the pressureless, sintering temperature was raised to 1250° C. (from 1235° C.) to ensure that all ceramic parts reached closed porosity prior to subsequent HIPing. It is believed that the ceramic parts and physical properties produced under these modified conditions do not differ appreciably from those described in Example 1. Rather, it is believed that it is the typical scale-up, "mass" effects (e.g., air flow and/or thermal effects) that require the extension of burn-out time and the increase in sintering temperature to ensure uniform processing results.

Properties and additional characterization of Example 3 Translucent Alumina are included below.

In order to compare the translucent alumina materials of this invention with commercially available translucent and opaque aluminas, the following comparative examples were characterized as described below.

Comparative Example A

Figure 5:
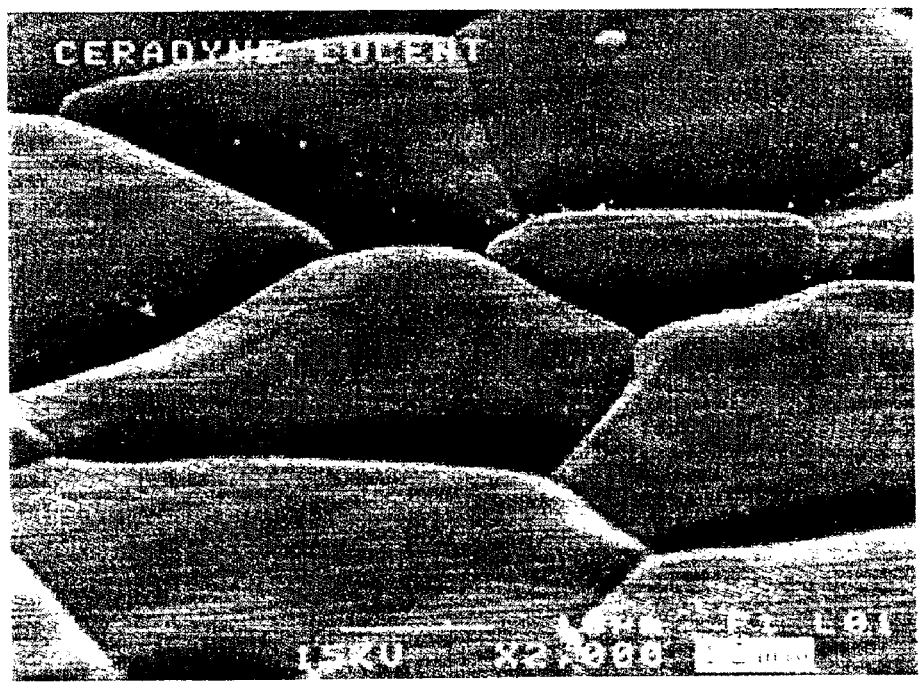
FIG. 5 is an SEM image (2,000x) of a cross-section of the Comparative Example A ceramic material.

Comparative Example A is a translucent alumina available from Ceradyne, Inc., Costa Mesa, Calif., and sold under the tradename TRANSTAR. The grain size of the TRANSTAR ceramic was measured according to the test method provided herein and found to be 30.0 microns. The hardness of the TRANSTAR ceramic was measured according to the test method provided herein and found to be 19.7±0.8 GPa. A Scanning Electron Microscopy image (2,000×) of Comparative Example A is shown in FIG. 5.

Comparative Example B

Comparative Example B is an opaque (ivory-colored) alumina, available under the trade designation of "998" from Vesuvius McDanel, Beaver Falls, Pa.

Comparative Example C

Comparative Example C is translucent alumina available from Ceradyne, Inc., and sold under the tradename "CERADYNE TPA." This material is used to produce the 3M CLARITY line of orthodontic brackets (3M Unitek, Monrovia, Calif.).

Comparative Example D

Comparative Example D is a commercially available translucent alumina orthodontic bracket, available under the trade designation of "CONTOUR Ceramic Brackets" from Class One Orthodontics, Lubbock, Tex.

Comparative Example E

Comparative Example E is a commercially available translucent alumina orthodontic bracket, available under the trade designation of "MXi" from TP Orthodontics, Inc., LaPorte, Ind.

Test Evaluations and Results

In order to compare the fine-grained translucent alumina materials of the present invention with other commercially available aluminas, the characterization outlined below was completed. This work compared the translucent alumina of the present invention to both coarse- and fine-grained translucent alumina as well as to coarse-grained opaque alumina.

Flexure Strength

Flexure Strength was measured according to the Test Method described herein and the test results for Example 1 and Comparative Examples A and B are reported in Table 1.

TABLE 1

| | Flexure Strength | | |
|---|---|---|---|
| Sample | Average Strength MPa (Standard Deviation) | Maximum Strength MPa | Minimum Strength MPa |
| Example 1 | 620 (161) | 817 | 366 |
| Comparative Ex. A | 280 (32) | 321 | 234 |
| Comparative Ex. B | 340 (24) | 377 | 310 |

The results in Table 1 indicate that the Flexure Strength of the Example 1 translucent alumina is approximately 2 times that of the Comparative Example A translucent material. It should be noted that the large standard deviation in the Example 1 values likely resulted from the difficulties experienced in machining this material. The fine-grained structure and high strength/hardness made defect-free machining of Example 1 flexure bars very challenging. However, the demonstrated strength of Example 1 may allow smaller, less bulky translucent articles to be constructed from such material.

Translucency: Contrast Ratio

In order to quantitatively assess the translucency of ceramic samples, Contrast Ratio was measured according to the Test Method described herein and the test results for Example 3, and Comparative Examples A and B are reported in Table 2.

TABLE 2

| | Translucency |
|---|---|
| Sample | Contrast Ratio |
| Example 3 | 0.307 |
| Comparative Ex. A | 0.513 |
| Comparative Ex. B | 0.983 |

The results in Table 2 indicate that the translucency of the Example 3 Alumina exceeds that of the Comparative Example A material and thus would be very suitable for highly aesthetic dental articles, e.g., dental prostheses or orthodontic brackets, that allow natural tooth color to diffusely show through the article. This result was surprising in that it had been previously reported (e.g., U.S. Pat. No. 4,954,080) that if the average grain size of a ceramic appliance was less than about two microns, then optical effects due to adjacent grain boundaries might interfere with good light transmission through the appliance.

Hardness and Grain Size Comparison of Ceramic Samples

Figure 6A:
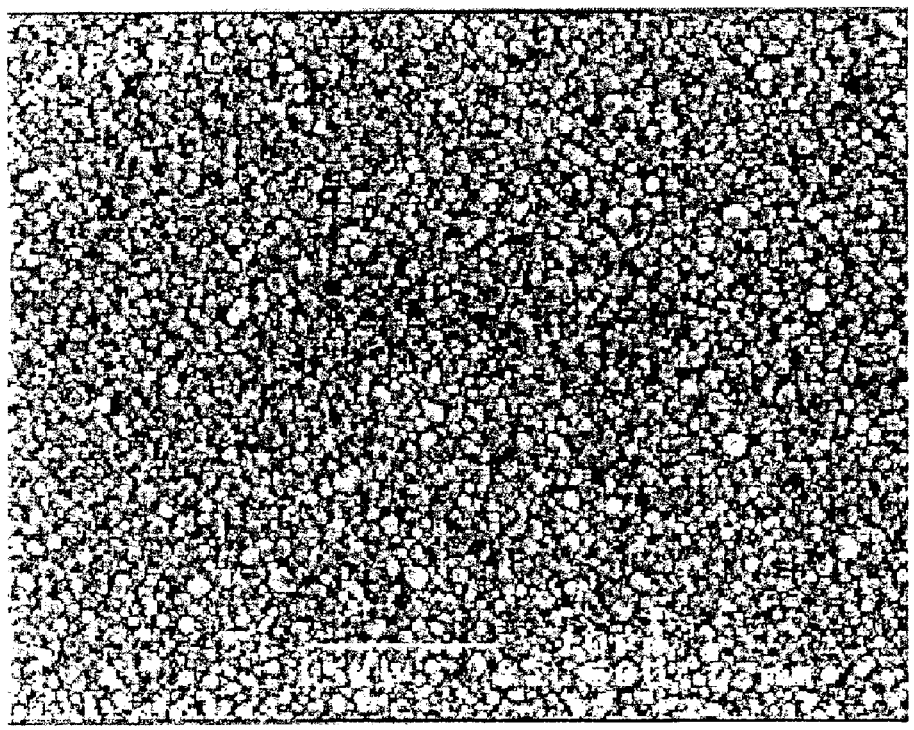
FIG. 6a is an SEM image (2,500x) of a cross-section of the Example 3 ceramic material.
Figure 6B:
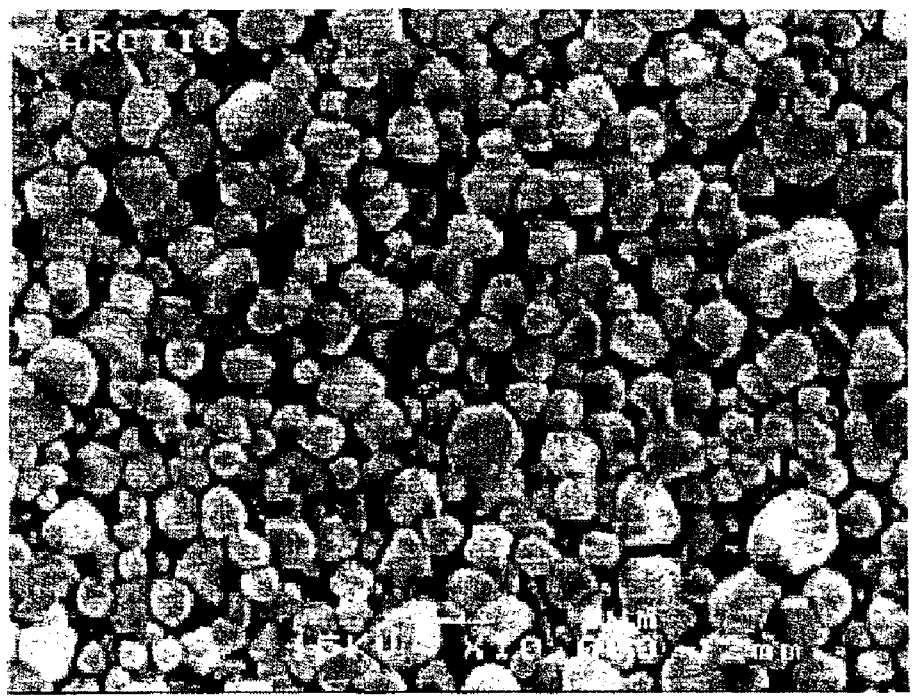
FIG. 6b is an SEM image (1,000x) of a cross-section of the Example 3 ceramic material.
Figure 7:
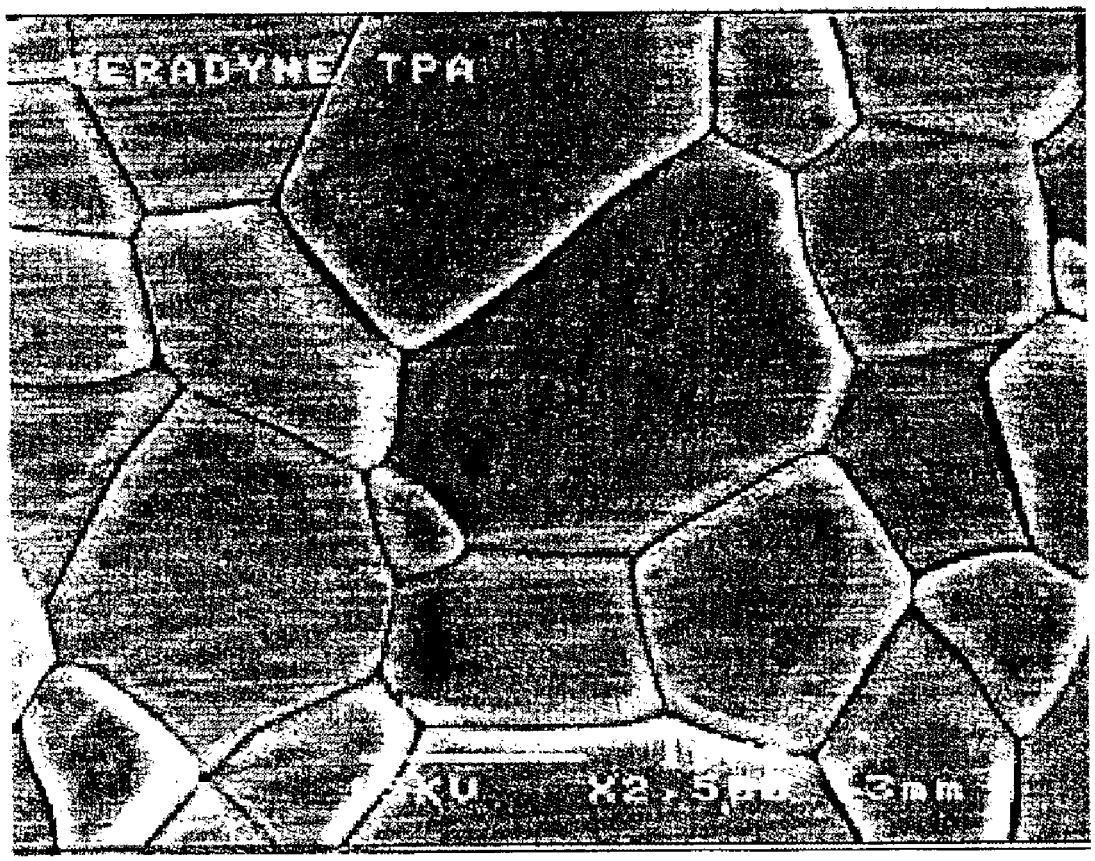
FIG. 7 is an SEM image (2,500x) of a cross-section of the Comparative Example C ceramic material.
Figure 8A:
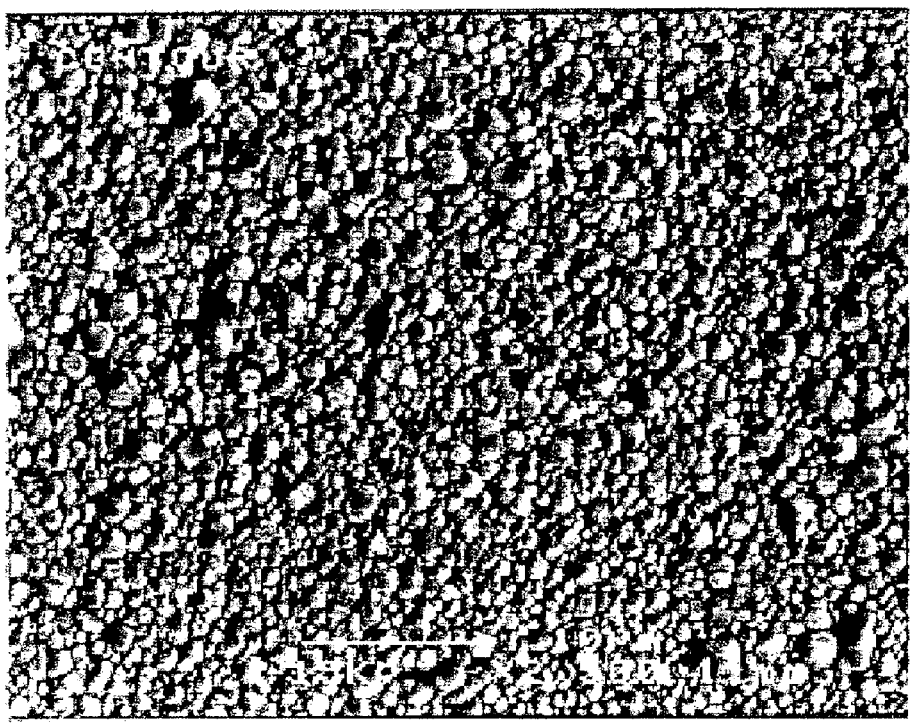
FIG. 8a is an SEM image (2,500x) of a cross-section of the Comparative Example D ceramic material.
Figure 8B:
FIG. 8b is an SEM image (10,000x) of a cross-section of the Comparative Example D ceramic material.
Figure 9A:
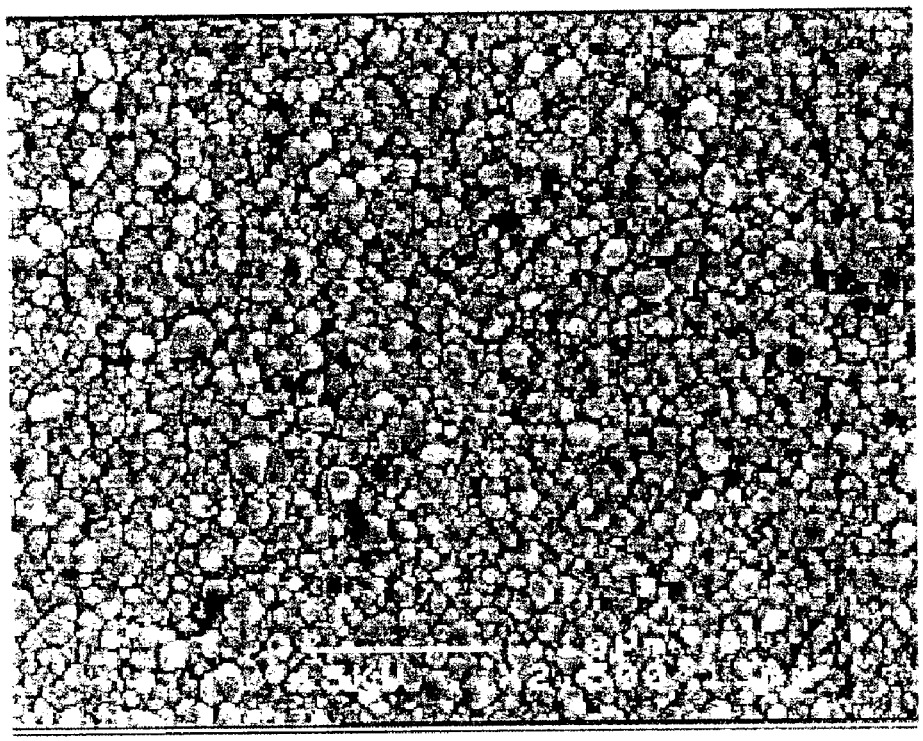
FIG. 9a is an SEM image (2,500x) of a cross-section of the Comparative Example E ceramic material.
Figure 9B:
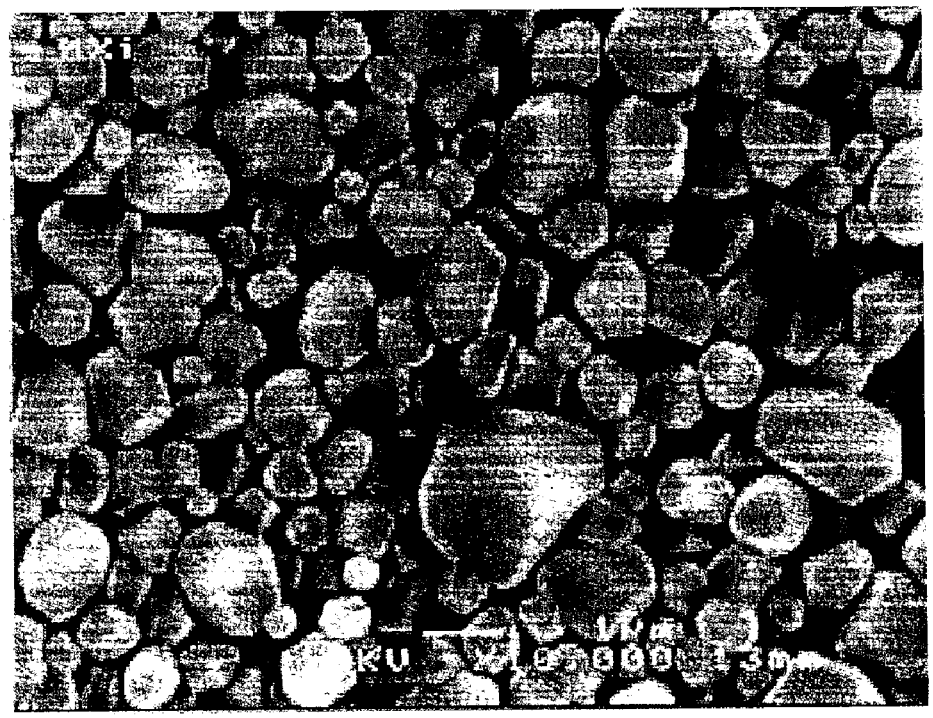
FIG. 9b is an SEM image (10,000x) of a cross-section of the Comparative Example E ceramic material.

Hardness and Grain Size were determined according to the Test Methods described herein and the results for Example 3, Comparative Example C, and the two bracket samples (Comparative Examples D and E) are reported in Table 3. Examples of the SEM images (2,500× and 10,000×) used to determine the average grain sizes of the Example 3, Comparative Example C, Comparative Example D, and Comparative Example E samples are shown in FIGS. 6a and 6b, FIG. 7 (2500× only), FIGS. 8a and 8b, and FIGS. 9a and 9b, respectively.

TABLE 3

Hardness and Grain Size of Ceramic Samples

| Bracket Sample | Hardness (GPa) | Grain Size (Microns) |
| --- | --- | --- |
| Example 3 | 20.9 ± 0.8 | 0.8 |
| Comparative Ex. C | 17.1 ± 0.6 | 15.3 |
| Comparative Ex. D | 20.5 ± 0.5 | 1.3 |
| Comparative Ex. E | 20.0 ± 0.5 | 1.2 |

The results in Table 3 indicate that the hardness of the Example 3, Comparative Example D, and Comparative Example E samples are statistically equivalent and that all three of these "fine-grained" samples have larger hardness values (and therefore may be expected to be stronger) than the "coarser-grained" Comparative Example C sample. The average grain size of the Comparative Example C sample was about 18 times larger than the Example 3 sample. The average grain sizes of the Comparative Example D and E samples were similar and about 50% larger than the Example 3 sample. Additionally, it is clear from the SEM images (FIGS. 6a, 6b, 8a, 8b, 9a, and 9b) that the Example 3 grains appeared visually to be more uniform or unimodal in size, while the Comparative Example D and E samples had a broader, distribution of grain sizes, with a greater number of larger single grains. Because of the smaller and more uniform grain composition of the Example 3 sample, articles constructed from this material would be expected to have improved physical and mechanical properties.

It should be noted that grain sizes different than those stated above for the Comparative Examples D and E materials have been previously reported (Giao (Robert) Ngoc Pham, "Fracture Characteristics, Hardness, and Grain Size of Five Polycrystalline Alumina Orthodontic Brackets," Ohio State University Master's thesis, 1999). In that report Pham states that the "grain size" of Comparative Example D (CONTOUR) is 0.57 microns and that the "grain size" of Comparative Example E (MXi) is 0.65 microns. However, both Pham and the reference he cites describing his "grain size" measurement technique, (L. H. Van Vlack, "Elements of Materials Science and Engineering," $6^{th}$ Edition, 217–219, 1989) state, "The mean chord length, L, is an index of grain size." As noted above, this mean chord or intercept length must be multiplied by a proportionality constant to determine an actual grain size. However, Pham goes on to report this index of grain size (chord length) as the actual grain size, without multiplying by the needed proportionality constant. Furthermore, the Van Vlack reference states that L is determined "by placing a random line of known length across a polished and etched microstructure," as was done in the technique described herein. However, Pham states, "Brackets of each brand were then notched with a diamond disk and fractured with a chisel. These fractured bracket halves were also mounted and coated with a gold-palladium film. The fracture surface morphology of each bracket was observed, and representative SEM photomicrographs were taken. The mean grain sizes of the five polycrystalline brackets were calculated directly from the SEM photomicrographs using a modified intercept method." The differences between examining a polished surface (as called for in the referenced standard) and a fractured surface (as Pham did), as well as Pham's failure to apply the proportionality constant, likely lead to the discrepancies in reported grain size for Comparative Examples D and E herein and in Pham's report.

Translucency: Bracket-Sized Samples

Figure 10:
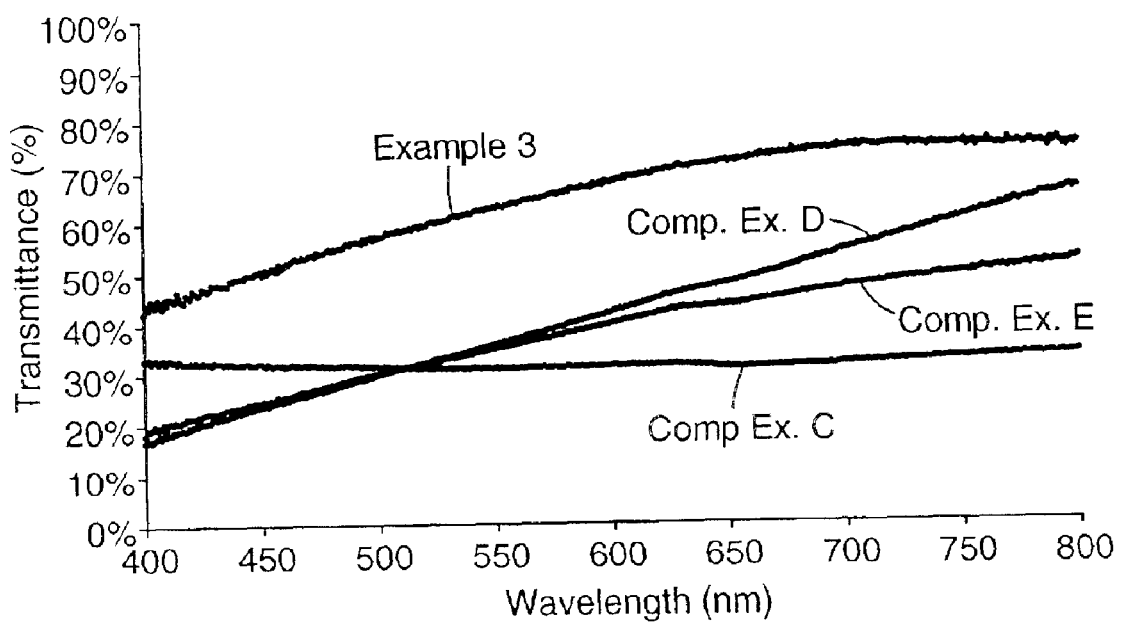
FIG. 10 is a graphical representation of Light Transmittance (%) versus Wavelength (nm) for Example 3, Comparative Example C, Comparative Example D, and Comparative Example E ceramic materials.

Translucency was determined according to the "Translucency of Small Samples (Wet Transmittance)" Test Method described herein and the results for Example 3, and Comparative Examples C, D and E are reported in tabular form (Table 4) as well as in graphical form (FIG. 10).

TABLE 4

Translucency of Bracket-Sized Samples

| Bracket Sample | Wet Transmittance (%) | Wavelength (nm) |
| --- | --- | --- |
| Example 3 | 42 | 400 |
|  | 57 | 500 |
|  | 68 | 600 |
|  | 74 | 700 |
|  | 75 | 800 |
| Comparative Ex. C | 33 | 400 |
|  | 31 | 500 |
|  | 31 | 600 |
|  | 32 | 700 |
|  | 34 | 800 |
| Comparative Ex. D | 17 | 400 |
|  | 30 | 500 |
|  | 42 | 600 |
|  | 54 | 700 |
|  | 66 | 800 |
| Comparative Ex. E | 18 | 400 |
|  | 30 | 500 |
|  | 40 | 600 |
|  | 47 | 700 |
|  | 52 | 800 |

The results in Table 4 and FIG. 10 indicate that the Example 3 sample is appreciably more translucent than the other three materials. The wet transmittance of the Example 3 sample is about 2 times greater than the wet transmittance of Comparative Example D and E samples at lower wavelengths and 20–50% greater at longer wavelengths. The integrated area under a wet transmittance vs wavelength curve, another measure of the translucency of these materials, is reported in Table 5 (in units of Percent Wet Transmittance×Light Wavelength (nm) or % T-nm).

TABLE 5

Integrated Translucency (between 475 and 650 nm)

| Sample | Integrated Wet Transmittance (% T-nm) |
| --- | --- |
| Example 3 | 110 |
| Comparative Example C | 55 |
| Comparative Example D | 65 |
| Comparative Example E | 62 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A polycrystalline translucent aluminum oxide ceramic material having an average grain size of no greater than 1.0 micron as measured on a polished surface and a Contrast Ratio value of less than about 0.7.

2. The polycrystalline translucent ceramic material of claim 1 wherein no greater than 10% of the grains of a polished surface of the material has a largest dimension greater than 1.0 micron.

3. The polycrystalline translucent ceramic material of claim 1 having a wet transmittance of at least about 40% at about 550 nm.

4. The polycrystalline translucent ceramic material of claim 3 having a wet transmittance of at least about 50% at about 650 nm.

5. The polycrystalline translucent ceramic material of claim 1 wherein a wet transmittance curve over a range of about 475 nm to about 650 nm has an integrated area of greater than about 70%T-nm.

6. The polycrystalline translucent ceramic material of claim 1 wherein the material has a Contrast Ratio value of less than about 0.5.

7. The polycrystalline translucent ceramic material of claim 6 wherein the material has a Contrast Ratio value of less than about 0.4.

8. The polycrystalline translucent ceramic material of claim 1 having a flexure strength of at least about 400 MPa.

9. The polycrystalline translucent ceramic material of claim 8 having a flexure strength of at least about 600 MPa.

10. The polycrystalline translucent ceramic material of claim 1 having a purity of at least about 99.5 wt-%.

11. The polycrystalline translucent ceramic material of claim 10 comprising up to about 0.5 wt-% of magnesium oxide, yttrium oxide, zirconium oxide, hafnium oxide, calcium oxide, or combinations thereof.

12. The polycrystalline translucent ceramic material of claim 1 wherein the material is in the form of a dental article, an infrared radar dome, a sodium vapor lamp envelope, a window, or military armor.

13. The polyciystalline translucent ceramic material of claim 12 wherein the material is in the form of a dental article.

14. The polycrystalline translucent ceramic material of claim 13 wherein the dental article is a dental prosthesis.

15. The polycrystalline translucent ceramic material of claim 14 wherein the dental prosthesis is selected from the group consisting of a crown, a coping, a bridge framework, a dental implant, a dental implant abutment, an inlay, an onlay, and a veneer.

16. A dental mill blank comprising a polycrystalline translucent aluminum oxide ceramic material having an average grain size of no greater than 1.0 micron and a Contrast Ratio value of less than about 0.7.

17. The dental mill blank of claim 16 wherein the blank is mounted to a holder selected from the group of a stub, a frame, a collett, and a plate.

18. The dental mill blank of claim 16 wherein the ceramic material has a tooth-like shade.

19. The dental mill blank of claim 16 wherein no greater than 10% of the grains of a polished surface of the ceramic material has a largest dimension greater than 1.0 micron.

20. The dental mill blank of claim 16 wherein the ceramic material has a wet transmittance of at least about 40% at about 550 nm.

21. The dental mill blank of claim 20 wherein the ceramic material has a wet transmittance of at least about 50% at about 650 nm.

22. The dental miil blank of claim 16 wherein a wet transmittance curve of the ceraniic material over a range of about 475 nm to about 650 nm has an integrated area of greater than about 70%T-nm.

23. The dental mill blank of claim 16 wherein the ceramic material has a Contrast Ratio value of less than about 0.5.

24. The dental mill blank of claim 23 wherein the ceramic material has a Contrast Ratio value of less than about 0.4.

25. The dental mill blank of claim 16 wherein the ceramic material has a flexure strength of at least about 400 MPa.

26. The dental mill blank of claim 25 wherein the ceramic material has a flexure strength of at least about 600 MPa.

27. The dental mill blank of claim 16 wherein the ceramic material has a purity of at least about 99.5 wt-%.

28. The dental mill blank of claim 16 wherein the ceramic material comprises up to about 0.5 wt-% of magnesium oxide, yttrium oxide, zirconium oxide, hafnium oxide, calcium oxide, or combinations thereof.

29. A ceramic dental prosthesis comprising a polycrystalline translucent aluminum oxide ceramic material having an average grain size of no greater than 1.0 micron and a Contrast Ratio value of less than about 0.7.

30. The prosthesis of claim 29 wherein the ceramic material is coated at least partially with an aesthetic coating material selected from the group consisting of porcelain, glass. glass-ceramic, composite, resin ceramic composite, and combinations thereof.

31. The prosthesis of claim 29 wherein the prosthesis is attached to tooth structure with dental cement.

32. The prosthesis of claim 29 wherein no greater than 10% of the grains of a polished surface of the ceramic material has a largest dimension greater than 1.0 micron.

33. The prosthesis of claim 29 wherein the ceramic material has a wet transmittance of at least about 40% at about 550 nm.

34. The prosthesis of claim 29 wherein the ceramic material has a wet transmittance of at least about 50% at about 650 nm.

35. The prosthesis of claim 29 wherein a wet transmittance curve of the ceramic material over a range of about 475 nm to about 650 nm has an integrated area of greater than about 70%T-nm.

36. The prosthesis of claim 29 wherein the ceramic material has a Contrast Ratio value of less than about 0.5.

37. The prosthesis of claim 36 wherein the ceramic material has a Contrast Ratio value of less than about 0.4.

38. The prosthesis of claim 29 wherein the ceramic material has a flexure strength of at least about 400 MPa.

39. The prosthesis of claim 38 wherein the ceramic material has a flexure strength of at least about 600 MPa.

40. The prosthesis of claim 29 wherein the ceramic material has a purity of at least about 99.5 wt-%.

41. The prosthesis of claim 29 wherein the ceramic material comprises up to about 0.5 wt-% of magnesium oxide, yttrium oxide, zirconium oxide, hafnium oxide, calcium oxide, or combinations thereof.

42. A kit comprising:
   a dental mill blank comprising a polycrystalline translucent aluminum oxide ceramic material having an average grain size of no greater than 1.0 micron and a Contrast Ratio value of less than about 0.7; and
   instructions for using the mill blank.

43. The kit of claim 42 further comprising a component selected from the group consisting of a bonding agent, a milling lubricant, a color-matching composition suitable for use in the oral environment, an impression material, an instrument, a dental composite, a dental porcelain, an abrasive, and combinations thereof.

44. A method for making a polycrystalline translucent aluminum oxide ceramic material having an average grain size of no greater than 1.0 micron as measured on a polished surface and a Contrast Ratio value of less than about 0.7, the method comprising:
   providing an aluminum oxide powder;
   forming the powder into an article having a desired shape;
   sintering the shaped article to obtain a sintered article having closed porosity; and subjecting the sintered article to hot isostatic pressing to further densify and form a densified article comprising polycrystalline translucent aluminum oxide ceramic material having an average grain size of no greater than 1.0 micron as measured on a polished surface and a Contrast Ratio value of less than about 0.7.

45. The method of claim 44 further comprising deagglomerating the aluminum oxide powder prior to forming the powder into an article having a desired shape.

46. The method of claim 45 wherein deagglomerating the aluminum oxide powder comprises subjecting the aluminum oxide powder to ultra-sonication.

47. The method of claim 44 wherein subjecting the sintered article to hot isostatic pressing comprises subjecting the sintered article to hot isostatic pressing at a temperature of about 1200° C. to about 1300° C. for about 30 minutes to about 120 minutes under about 100 MPa to about 210 MPa of an inert gas.

48. The method of claim 44 wherein forming the powder into an article having a desired shape comprises forming a mill blank comprising ceramic material in a green stage.

49. The method of claim 48 further comprising carving the green-stage mill blank into a desired shape prior to sintering the shaped article to obtain a sintered article having closed porosity.

50. The method of claim 44 further comprising carving the sintered article having closed porosity into a desired shape prior to subjecting the sintered article to hot isostatic pressing to further densify.

51. The method of claim 44 further comprising carving the densified article into a desired shape.

52. The method of claim 44 wherein forming the powder into an article having a desired shape comprises shiny casting the aluminum oxide powder.

53. The method of claim 44 wherein forming the powder into an article having a desired shape comprises injection molding the aluminum oxide powder.

54. The method of claim 44 wherein the aluminum oxide powder has a surface area of greater than about 10 $m^2/g$.

55. The method of claim 54 wherein the aluminum oxide powder has a surface area of greater than about 14 $m^2/g$.

56. The method of claim 44 wherein the aluminum oxide powder has a purity of at least about 99.5%.

57. The method of claim 44 wherein the densified article is a dental mill blank.

58. The method of claim 44 wherein the densified article is a dental prosthesis.

59. A method for making a dental prosthesis comprising:
providing a dental mill blank comprising a polycrystalline translucent aluminum oxide ceramic material having an averane grain size of no greater than 1.0 micron and a Contrast Ratio value of less than about 0.7; and
carving the mill blank into a desired shape.

60. The method of claim 59 further comprising attaching the carved blank to tooth or bone structure.

61. The method of claim 60 wherein the carved blank is attached to the tooth or bone structure with a color-matching bonding agent.

* * * * *

UNITED STATES PATENT AND TRADEMARK OFFICE
CERTIFICATE OF CORRECTION

PATENT NO. : 6,878,456 B2
DATED : April 12, 2005
INVENTOR(S) : Castro, Darren T.

It is certified that error appears in the above-identified patent and that said Letters Patent is hereby corrected as shown below:

Title page,
Item [56], References Cited, OTHER PUBLICATIONS, "Jeppesen" reference, after "Thermo-Optical" insert -- , --.

Column 3,
Line 51, delete "(1,000x)" and insert -- (10,000x) --, therefor.

Column 18,
Line 32, delete "20-50%" and insert -- 25-50% --, therefor.

Column 19,
Line 30, delete "polyciystalline" and insert -- polycrystalline --, therefor.
Line 58, delete "miil" and insert -- mill --, therefor.
Line 59, delete "ceraniic" and insert -- ceramic --, therefor.

Column 20,
Line 16, after "glass" (1$^{st}$ Occurrence) delete "." and insert -- , --, therefor.

Column 22,
Line 2, delete "shiny" and insert -- slurry --, therefor.
Line 21, delete "averane" and insert -- average --, therefor.

Signed and Sealed this

Thirtieth Day of August, 2005

JON W. DUDAS
*Director of the United States Patent and Trademark Office*